United States Patent [19]

Hochstein

[11] 4,433,693

[45] Feb. 28, 1984

[54] METHOD AND ASSEMBLY FOR MONITORING RESPIRATION AND DETECTING APNEA

[76] Inventor: Peter A. Hochstein, 14020 Fifteen Mile Rd., Sterling Heights, Mich. 48077

[21] Appl. No.: 259,590

[22] Filed: May 1, 1981

Related U.S. Application Data

[60] Division of Ser. No. 79,457, Sep. 27, 1979, Pat. No. 4,279,253, which is a continuation-in-part of Ser. No. 783,168, Mar. 31, 1977, abandoned, which is a continuation-in-part of Ser. No. 598,934, Jul. 25, 1975, abandoned.

[51] Int. Cl.³ ............................................. A61B 5/08
[52] U.S. Cl. ..................................... 128/721; 128/722
[58] Field of Search ............................... 128/721–722, 128/748, 774, 903, 653, 631

[56] References Cited

U.S. PATENT DOCUMENTS

| | | | |
|---|---|---|---|
| 3,942,513 | 3/1976 | Frank | 128/721 |
| 3,943,915 | 3/1976 | Severson . | |
| 3,958,558 | 5/1976 | Dunphy et al. . | |
| 4,114,606 | 9/1978 | Seylar | 128/653 |
| 4,252,129 | 2/1981 | Tamura et al. | 128/903 X |
| 4,308,872 | 1/1982 | Watson et al. | 128/721 X |

OTHER PUBLICATIONS

Zerkin, M., "A Pediatric Belly Belt Respiration Monitor", Annual Conference on Engr. in Med. & Biol., 29th ACEMB Boston Mass, 6-10, Nov. 1976, p. 333.
Delchor, T. A. et al., "An Improved Method for Detecting Passive Pills", Phys. in Med. & Biol. vol. 21, #4, pp. 577–588, Jul. 1976.

*Primary Examiner*—Kyle L. Howell
*Assistant Examiner*—Francis J. Jaworski
*Attorney, Agent, or Firm*—Harold W. Milton, Jr.

[57] ABSTRACT

A method and assembly for monitoring respiration and detecting apnea. The assembly includes an oscillator for generating an electromagnetic field having an output frequency in the radio frequency range and a high Q passively tuned LC circuit which has a resonant frequency variable in the radio frequency range generated by the oscillator. The LC circuit responds to the electromagnetic field by absorbing electromagnetic energy from the field when the resonant frequency matches the output frequency of the oscillator. A band is positioned about the subject's chest or abdominal cavity to vary the resonant frequency of the LC circuit in response to the expansion and contraction of the subject's chest or abdominal cavity. A detecting means is also provided for detecting when the LC circuit is responsive to the electromagnetic field established by the oscillator. In one embodiment the output frequency of the electromagnetic field established by the oscillator is maintained constant and the detecting means includes reset timing means for providing a signal when the LC circuit fails to respond to the electromagnetic field within a predetermined time period. In a second embodiment the output frequency of the electromagnetic field established by the oscillator is varied within the predetermined frequency range and the detecting means includes reset timing means for providing a signal when the LC circuit fails to respond to the electromagnetic field at different resonant frequencies within the predetermined frequency range within a predetermined time period.

8 Claims, 14 Drawing Figures

METHOD AND ASSEMBLY FOR MONITORING RESPIRATION AND DETECTING APNEA

This application is a divisional of application Ser. No. 79,457 now U.S. Pat. No. 4,279,253, filed Sept. 27, 1979 which is a continuation-in-part of application Ser. No. 783,168, filed Mar. 31, 1977 and now abandoned which, in turn, is a continuation-in-part of application Ser. No. 598,934, filed July 25, 1975 now abandoned.

BACKGROUND OF THE INVENTION

1. Field of the Invention

Although the present invention has wider utility, it particularly relates to a method and assembly for monitoring respiration and detecting apnea in a human subject.

Apnea or the transient cessation of respiration may occur unexpectedly and tragically in infants up to the age of 3 years. It is a leading killer of infants between the ages of 1 month and 1 year, as it strikes thousands of homes every year. The cause of this mysterious killer in infants has not yet been discovered.

This killer is aptly called crib death or sudden infant death syndrome because the syndrome always seems to strike during sleep and has been found to take the lives of infants in such closely supervised environments as hospitals.

One new focal point of study in this area has been directed to the infant's central nervous system. It is known that an infant's nervous system is developed in an orderly step-by-step fashion as fetal reflexes are systematically replaced by normal postnatal reflexes. It is possible that the timing of the replacement goes wrong in some infants, that is, the fetal reflexes decay before the postnatal system is fully developed or that it isn't replaced as scheduled and there are two systems working at once. Also, it is known that reflexes change during sleep, thereby altering the patterns of breathing, pulse rate and brain waves. As a result, it is possible that an underdeveloped system might simply fail to function during sleep resulting in spontaneous death.

2. Description of the Prior Art

There are many respiratory monitor systems which provide an electrical signal in response to the respiratory activity of infants. Such devices often measure by impedance pneumography or the tidal volume of the subject by a strain gauge taped directly on the abdomen of the subject. Optical breathing sensors and modulation of a high frequency carrier by a breathing sensor are also well known in monitoring respiration and detecting apnea.

Some of the problems inherent in the prior art respiration monitoring devices are: the inconvenience of bonding electrodes to the infant, the possible problem of shocking the infant with an electrical current and the problem of the human subject removing the sensor, either advertently or inadvertently.

INVENTION ADVANTAGES

The present invention avoids many of the above-noted problems in its use of remote monitoring with a passive circuit means i.e., all of the elements of the circuit are passive or, in other words, none of the circuit elements provided will exhibit an open current terminal voltage or a short circuit current when the terminals are short circuited. The passive circuit is placed about the infant's chest by means of a band and the infant is thereafter placed within a radio frequency electromagnetic field. In this way, the passive circuit means is thereby coupled through the electromagnetic field to an oscillator and coil which establish the electromagnetic field.

The present system is inherently fail-safe in that an inoperable passive circuit means, loss of coupling (i.e., the infant falls out of the crib in which the electromagnetic field exists) or respiratory malfunction results in an alarm signal which is latched "on" until it is reset.

The expansion and contraction of the infant's chest varies the resonant frequency of the passive circuit means which is tuned such that the resonant frequency of the passive circuit means coincides with or matches the output frequency of the electromagnetic field whenever the child breathes thereby resulting in intermittently increased coupling between the passive circuit and the oscillator. Loss of intermittently increased coupling is detected and produces a signal in the event of the cessation of breathing for a predetermined time period.

SUMMARY OF THE INVENTION

The present invention provides an assembly suitable for use in monitoring respiration and detecting apnea in a subject. A generating means generates an electromagnetic field having an output frequency in a predetermined frequency range about the subject. A passive circuit means having a resonant frequency variable in the predetermined frequency range is responsive to the electromagnetic field when the resonant frequency matches the output frequency. A transducer means adapted for attachment to the subject are provided for varying the resonant frequency of the passive circuit means in response to the force exerted on the transducer means by the expansion and contraction of that portion of the subject which normally expands and contracts during breathing.

The invention may include detecting means responsive to the generating means for detecting when the passive circuit is responsive to the electromagnetic field.

In one embodiment, the output frequency of the electromagnetic field is maintained constant and the detecting means includes reset timing means for providing a signal when the passive circuit fails to respond to the electromagnetic field within a predetermined time period and for reestablishing the predetermined time period upon each occurrence of the passive circuit being responsive to the electromagnetic field whereby the signal is provided in the event the subject fails to breath within the predetermined period.

In another embodiment, the output frequency of the electromagnetic field is varied within the predetermined frequency range and the detecting means includes reset timing means for providing a signal when the passive circuit fails to respond to the electromagnetic field at different resonant frequencies within the predetermined frequency range within a predetermined time period and for reestablishing the predetermined time period as the resonant frequency continues to vary within the predetermined frequency range whereby the signal is provided in the event the subject fails to breathe within the predetermined time period.

BRIEF DESCRIPTION OF THE DRAWINGS

Other advantages of the present invention will be readily appreciated as the same becomes better understood by reference to the following detailed description when considered in connection with the accompanying drawings wherein.

DESCRIPTION OF THE PREFERRED EMBODIMENTS

Although the subject invention has particular application in monitoring respiration and detecting apnea and will be described in connection with the best known modes of carrying out the invention, which is the monitoring of respiration and detecting apnea, it is understood that the invention has wider application by being useful to monitor forces or movement applied to a passive circuit responsive to an electromagnetic field.

Figure 2:
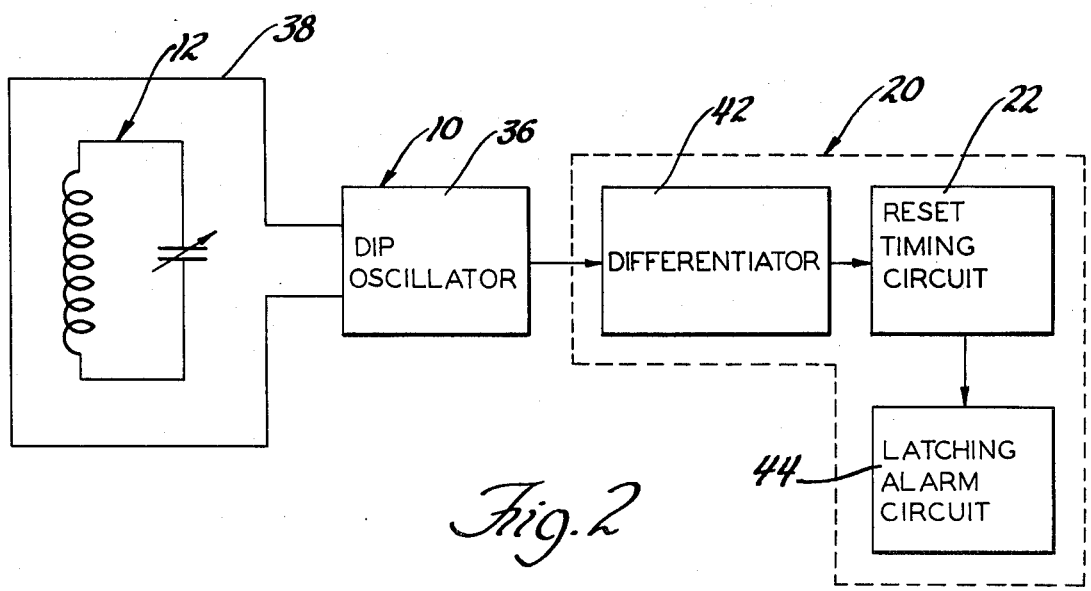
FIG. 2 is a block diagram showing the passive circuit means positioned within the plane of the coil means with the remainder of the block diagram representing the remaining circuit components of a first embodiment of the invention.
Figure 10:
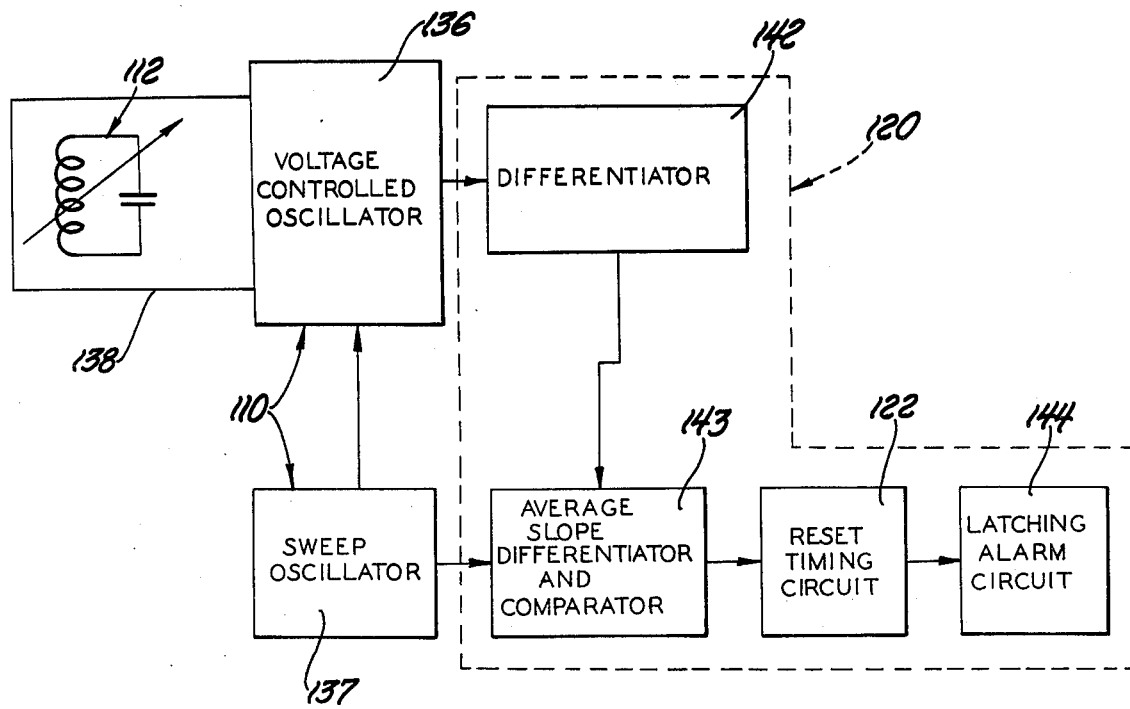
FIG. 10 is a block diagram showing the passive circuit means adjacent the coil means with the remainder of the block diagram representing the remaining circuit components of a second embodiment of the invention.

Two embodiments of the invention are illustrated and described herein with FIG. 2 schematically illustrating the first embodiment and FIG. 10 schematically illustrating the second embodiment. The first embodiment will be described followed by a description of the second embodiment.

Figure 1:
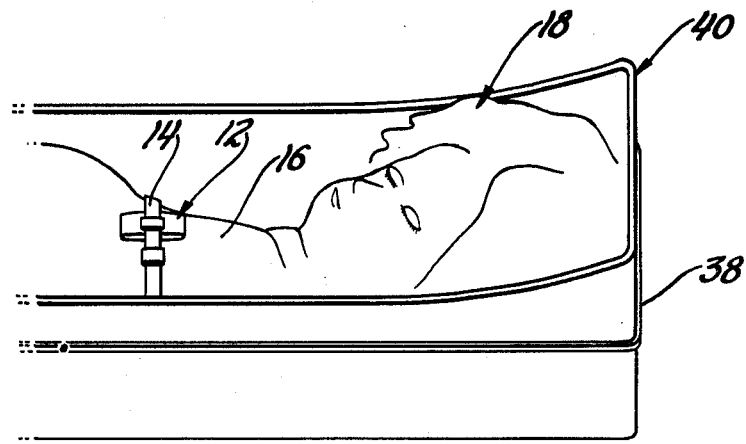
FIG. 1 is a perspective view of an infant with the passive circuit means and the transducer means mounted about the chest in a portion of the crib constructed with the coil means.
Figure 6:
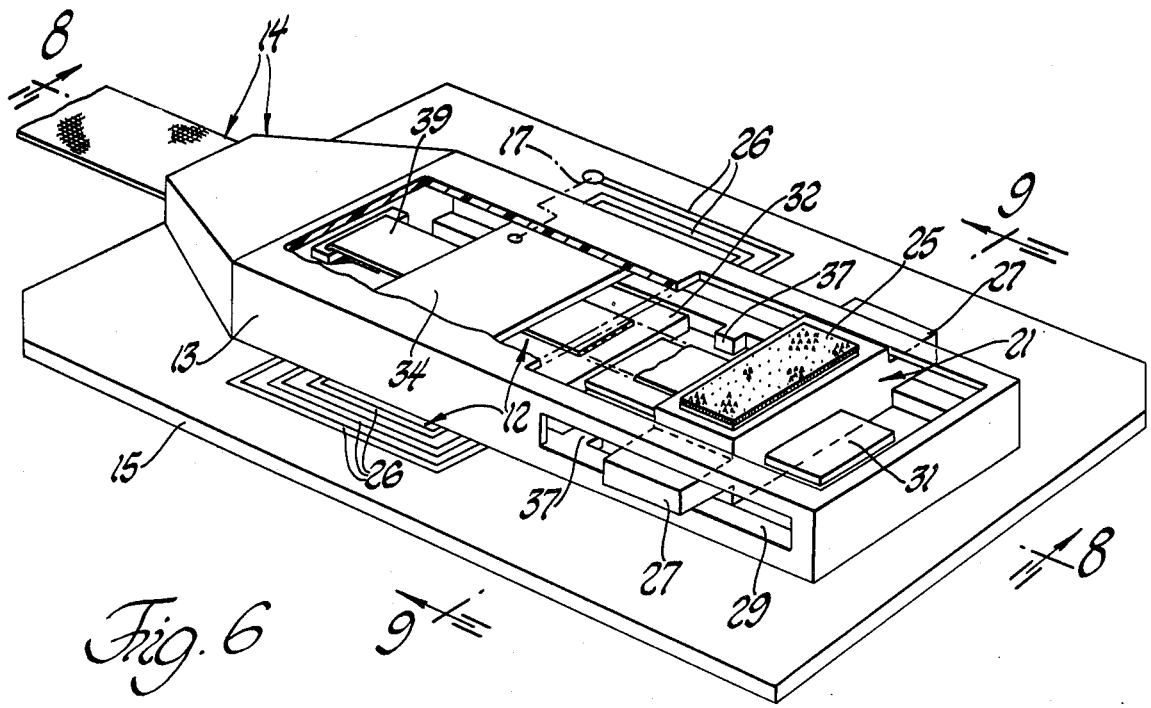
FIG. 6 is a perspective view partially cut away and in cross section of an assembly for responding to an electromagnetic field including a passive circuit means and a transducer or force transfer means.
Figure 7:
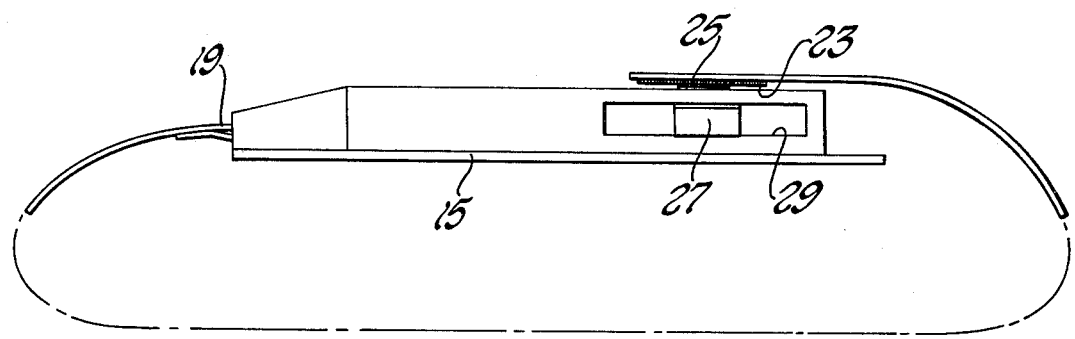
FIG. 7 is an elevational or side view of the assembly shown in FIG. 6.
Figure 8:
FIG. 8 is a cross-sectional view taken substantially along line 8—8 of FIG. 6.
Figure 9:
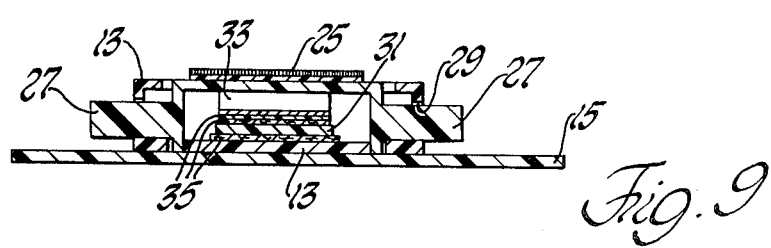
FIG. 9 is a cross-sectional view taken substantially along line 9—9 of FIG. 6.

A first assembly suitable for use in monitoring respiration and detecting apnea in a subject is shown generally in FIG. 2. A generating means generally indicated at 10 generates an electromagnetic field having an output frequency in a predetermined frequency range about the subject. A passive circuit means, generally indicated at 12, has a resonant frequency variable in the predetermined frequency range of the generating means 10. The passive circuit means 12 is responsive to the electromagnetic field when the resonant frequency matches the output frequency of the field. FIGS. 1 and 6 show transducer or force transfer means including a band 14 adapted for attachment to the subject for varying the resonant frequency of the passive circuit means 12 in response to the force exerted on the band 14 by the expansion and contraction of the chest 16 of the infant 18 during breathing.

Figure 5:
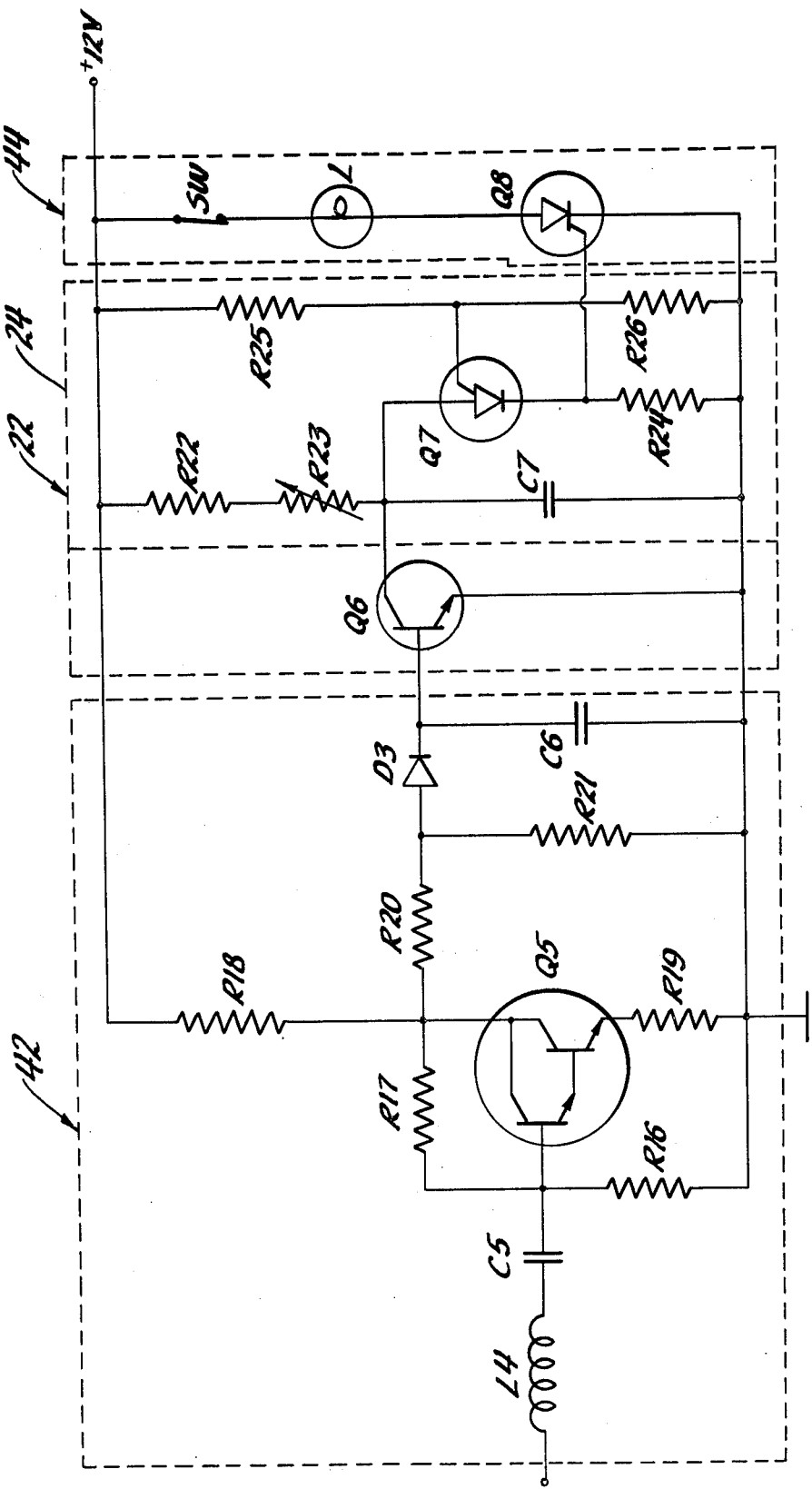
FIG. 5 is a schematic circuit diagram of the remainder of the comparison means of FIG. 4 of the reset timing means and the indicator means.

A detecting means, generally indicated at 20 in FIG. 2, is responsive to the generating means 10 and detects when the passive circuit means 12 is responsive to the electromagnetic field. In the first embodiment of FIG. 2, the output frequency of the electromagnetic field is maintained substantially constant. The detecting means 20 includes reset timing means such as reset timing circuit 22 which provides a first signal when the passive circuit means 12 fails to respond to the electromagnetic field within a predetermined time period. Reset timing circuit 22 also reestablishes the predetermined time period upon each occurrence of the passive circuit means 12 being responsive to the electromagnetic field. Thereby, an alarm signal is provided in the event the infant 18 fails to breathe within the predetermined time period Reset timing circuit 22 includes timer means 24, as shown in FIG. 5. This timer means 24 times out at the end of the predetermined time period and provides a first signal at the end of the predetermined time period. Typically, the predetermined time period will be equivalent to two or three normal breathing periods to prevent the emission of or generation of a false signal.

Figure 3:
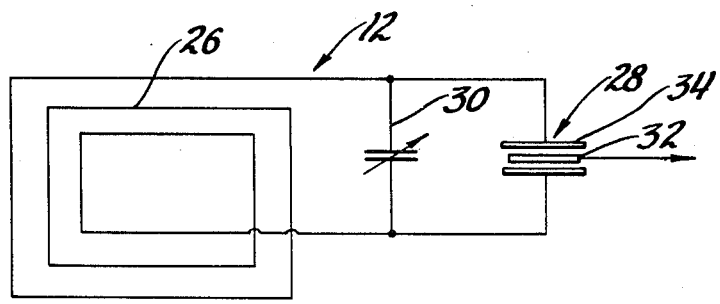
FIG. 3 shows the passive circuit means which includes a planar coil, a trimmer capacitor and a capacitive element with a movable dielectric.

As shown in FIG. 3, each element of the passive circuit means 12 is a passive element. That is, none of the circuit elements provided will exhibit an open current terminal voltage or short circuit current when the terminals are short circuited. The passive circuit means 12 includes at least one inductive means or element such as planar coil 26 and at least one capacitive means or element such as capacitor 28. The resonant frequency of the passive circuit means 12 is defined by the mathematical formula $\frac{1}{2\pi\sqrt{LC}}$, wherein L is the inductance of the planar coil in henries and C is the capacitance of the parallel combination of capacitor 28 and trimmer capacitor 30 in farads. Passive circuit means 12 is a high Q tuned resonant circuit, that is, it is a circuit with a high quality factor or Q designed to pass a narrow band of frequencies. A high value of Q indicates that for a given L and C the band width of the passive circuit means is small, thus making the passive circuit means 12 very frequency selective. In this particular embodiment of the invention planar coil 26 has a value of 2 microhenries, trimmer capacitor 30 has a nominal value of 30 picofarads and capacitor 28 has a nominal value of 10 picofarads. The trimmer capacitor functions as a "trimmer" to adjust the total capacity of the passive circuit. The passive circuit may be designed with the desired capacitance and inductance valves without requiring a trimmer capacitor 30. The trimmer capacitor is adjustable to "trim" or adjust the assembly so that the passive circuit passes back and forth through the resonant frequency (which is the same as the output frequency of the electromagnetic field) as the band moves the elements 32 and 34 relative to one another, i.e., the trimmer capacitor is an adjustment device, although it may not be included if the tolerances are closely held.

The capacitor 28 has a capacitance which is variable to thereby vary the resonant frequency of the passive circuit means 12 through the range. The capacitor 28 has a movable element of dielectric material 32 therein so that the position of the dielectric element 32 within the capacitor 28 determines the capacitance of the capacitor 28. The spacing of the capacitor plates may also be varied to change the resonant frequency of passive circuit means 12.

The expansion and contraction of chest 16 of baby 18 causes the band 14 which is positioned about the infant's chest to move the dielectric element 32 between the plates 34 of the capacitor 28. In this way, band 16 transmits the force exerted by chest 16 to the capacitor 28 of the passive circuit means 12 to reposition the dielectric element 32 between plates 34 to thereby vary the resonant frequency of the passive circuit means 12.

Referring to FIGS. 6 through 9 there is shown a specific embodiment of the passive circuit means 12 and the transducer or force transfer means 14. Said another way, FIG. 6 shows an assembly for responding to an electromagnetic field and includes the passive circuit means 12 having a resonant frequency variable in a predetermined frequency range of an electromagnetic field and being responsive to the electromagnetic field when the resonant frequency matches the frequency of the electromagnetic field. The assembly includes a force transfer means 14 for transferring forces from the object, such as the baby 18, to the passive circuit means 12 to vary the resonant frequency in the range of frequencies in which the passive circuit is resonant so that the passive circuit means responds to the frequency of the electromagnetic field.

The force transfer means 14 includes a body 13 disposed upon a substrate 15. The planar coil 26 is supported on the substrate plate 15 which forms a part of the passive circuit means 12. Also included in the passive circuit means 12 are upper and lower capacitor plates 34. The movable element 32 is made of dielectric material and is movably supported by the body 13 for movement parallel to and between the capacitor plates 34 to vary the capacitance of the capacitor. The planar coil 26 defines an inductive means and the capacitor plates 34 with the dielectric element 32 define a capacitive means. The coil 26 is electrically connected to the capacitor through electrical leads such as that shown at 17.

The force transfer means 14 also includes a force reaction means connected to the body 13 and to the movable element 32 for moving the movable element 32 in a first direction, to the right as viewed in FIG. 3, relative to the body in response to forces from the object such as the baby 18. More specifically, the force transfer means includes the strap attached at one end to the body 13, as indicated at 19, and a slip clutch means, generally indicated at 21, to which the opposite end of the strap is attached by the mechanically engaging pads 23 and 25 on the strap and the slip clutch means respectively. The slip clutch means 21 allows lost motion between the force reaction means, specifically the strap thereof, and the movable element 32 after a predetermined amount of movement of the movable element 32 or when there is a predetermined force resistance of the movement of the movable element 32. The slip clutch means includes a slide block having flanges 27 extending from the ends thereof and disposed in slots 29 in the body 13 for sliding movement relative to the body 13. A slip member 31 is connected to the movable element 32 and extends through the slide block. Friction means comprising the spring 33 and the friction pads 35 are disposed within the slide block to react between the slide block and the slip member 31 to prevent movement of the slip member 31 relative to the slide block until the movable element 32 moves a predetermined distance or amount. Specifically, the body 13 includes the stops 37 which limit the movement of the block 32.

Also included is a biasing means comprising an elastic strap 39 which operatively interconnects the body 13 and the slide block of the slip clutch means 21 for urging the element 32 to move in a direction opposite to the direction in which it is urged upon a force being applied thereto by the strap means through the slip clutch means 21.

In operation the assembly shown in FIGS. 6 through 9 may be placed upon an object by placing the strap in engagement therewith and within an electromagnetic field generated by the generating means. Upon a force being applied thereto through the strap the slip clutch means 21 is urged to move to the right as viewed in FIG. 8 and will move the movable dielectric element 32 to the right relative to the capacitor plates 34 thereby changing the capacitance of the capacitor and moving the passive circuit means through the range of frequencies in which it is resonant. Should the strap reacting with the body and the slip clutch means move the element 32 to engage the stops 37, the slip clutch body will move frictionally along the slip member 31 thereby preventing damage to the system. When the assembly is attached to an infant, upon each expansion of the chest the dielectric element 32 will move to the right, as viewed in FIG. 8, and when the chest cavity is reduced by exhaling the biasing means or strap 39 will move the element 32 back to the original position or to the left as viewed in FIG. 8 as it acts through the slip clutch body and the slip member 31. As the dielectric element 32 is moved between the capacitor plates 34 it changes the capacitance of the capacitor such that the passive circuit means becomes responsive to the frequency of the electromagnetic field being generated thereabout and the detecting means detects that the passive circuit is responsive.

Figure 4:
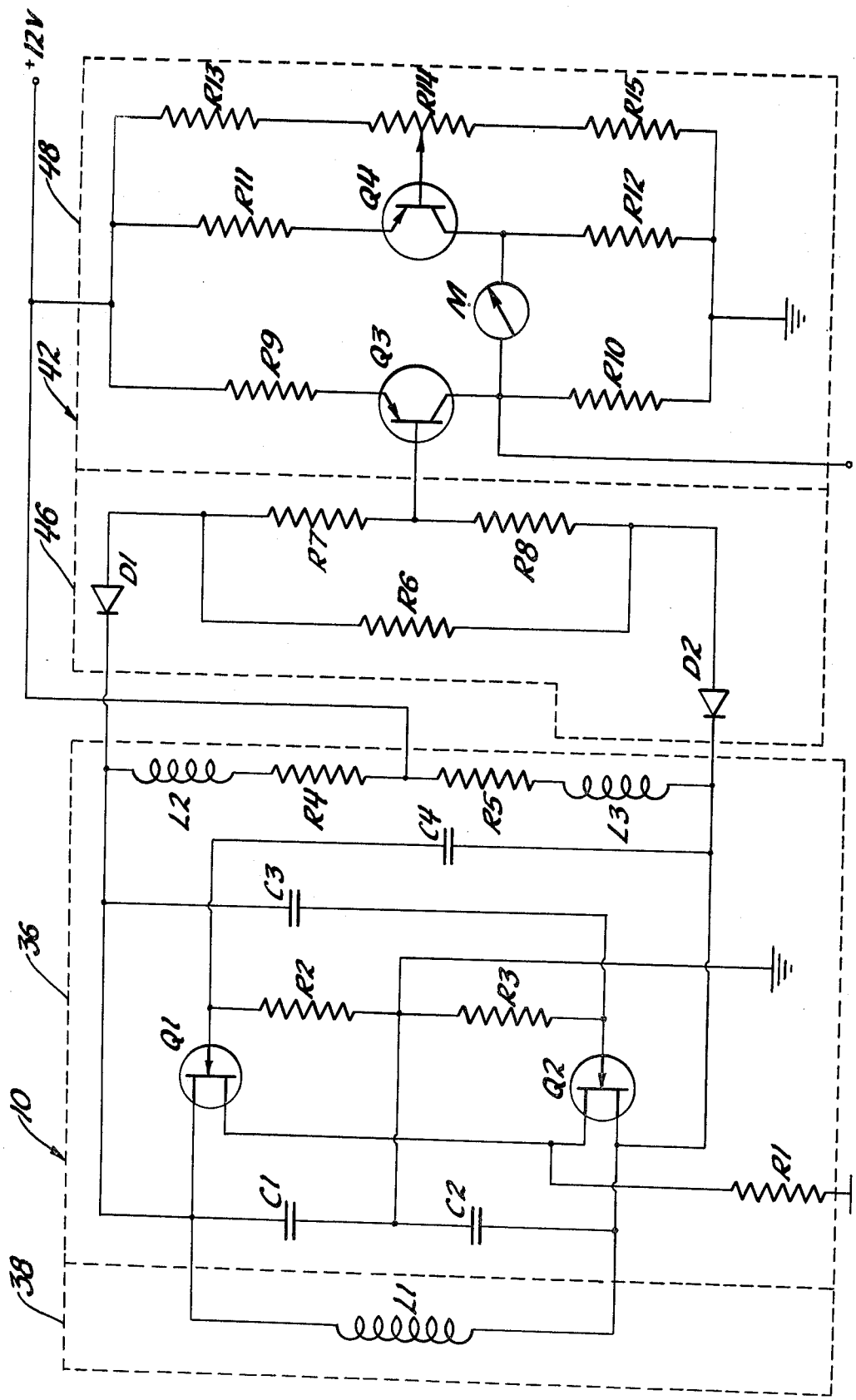
FIG. 4 is a schematic circuit diagram of the generating means and a portion of the comparison means of the detecting means.

The generating means 10 includes an oscillator means such as dip oscillator 36 and a coil means such as sensing coil 38 which is designated L1 in FIG. 4. The dip oscillator 36 oscillates at a predetermined constant frequency and the sensing coil 38 is coupled to the dip oscillator 36 so as to be responsive to the dip oscillator 36. When the passive circuit means 12 is coupled to the electromagnetic field generated by the generating means 10, the sensing coil 38 is coupled to the passive circuit means 12 by the electromagnetic field, as the coil 38 establishes the electromagnetic field about the passive circuit means 12. Coupling will be observed as an induced voltage in the planar coil 26 due to the action of Faraday's Law through flux linkages whose origin is sensing coil 38 positioned about the baby. As shown in FIG. 1, the sensing coil 38 is actually incorporated into baby crib 40 to thereby form an electromagnetic field within the baby crib 40.

The electromagnetic coupling between the passive circuit means 12 and the sensing coil 38 increases when the passive circuit means 12 is responsive to the electromagnetic field. That is, when the resonant frequency of the passive circuit means 12 is at or matches the output frequency of the generating means 10, the passive circuit means absorbs electromagnetic energy from the electromagnetic field.

The detecting means 20 includes comparison means such as differentiator 42 which is responsive to the increased coupling between the passive circuit means 12 and the sensing coil 38. Differentiator 42 compares the energy of the electromagnetic field before the increased coupling between the passive circuit means 12 and the sensing coil 38 to the energy of the electromagnetic field after the increased coupling, and generates a signal proportional to this difference.

The detecting means 20 further includes an indicator means such as a latching alarm circuit 44. The latching alarm circuit 44 provides an indication in response to the first signal provided by Q7. The latching alarm circuit 44 includes latching means such as silicon controlled rectifier Q8, for providing a second signal in response to the first signal provided by Q7. The latching alarm circuit 44 further includes an alarm means such as a light L and a switching means such as SW. Light L is responsive to the second signal and to switch SW.

Timing circuit 22 includes discharge means such as Q6 in FIG. 5. Q6 is a transistor which periodically discharges C7, the timing capacitor. The timer means 24 starts timing after Q6 has reset the timing capacitor C7 and thereby the timer means 24. The reset timing means provides a first signal when Q6 has failed to reset the timer means 24 within the predetermined time period. Differentiator 42 discharges Q6 when the passive circuit means 12 is responsive to the generating means 10. Differentiator 42 includes rectifying means 46, and a differential means such as differential amplifier 48. The rectifying means 46 produces or generates a direct voltage corresponding to the magnitude of the electromagnetic field, and the differential amplifier 48 amplifies small variations in the generated voltage which is subsequently differentiated by coupled capacitor C5 to discharge Q6.

Broadly, the dip oscillator 36 produces an output frequency of the electromagnetic field which is constant and may be referred to as an "interrogation" frequency. During breathing the passive circuit has its resonant frequency varied up and down through a range which includes the output frequency of the electromagnetic field. Each time the resonant frequency of the passive circuit coincides or matches with the output frequency of the electromagnetic field, a dip or decrease in oscillator current occurs. This dip is amplified and used to continually reset a timer which, in turn, actuates an alarm. Thus, the presence of a dip every few seconds indicate change in the resonant frequency of the passive circuit, i.e., breathing movement.

Referring now to FIG. 4, Q1 and Q2 are cross-coupled by C3 and C4 to oscillate at some predetermined frequency determined by C1 and C2 and the sensing coil L1. Both Q1 and Q2 are junction Field Effect Transistors. The radio frequency voltage level is monitored by rectifying the radio frequency voltage level with D1 and D2. D1 and D2 are Schottky diodes. The DC voltage component is then coupled to a differential stage which has a constant DC voltage level offset by R14. The differential stage includes Q3 and Q4 which are a differential pair of transistors. Additionally, a meter M, which can be a sensitive microammeter, is provided to visually detect dips in the current.

The circuit valves of the circuit elements shown in FIG. 4 are: L1—3 microhenries, C1—picofarads, C2—10 picofarads, R1—300 ohms, Q1 and Q2—Type E301 Transistor (siliconix) R2—10,000 ohms, R3—10,000 ohms, C3—5 picofarads, C4—5 picofarads, L2—22 microhenries, R4—51 ohms, R5—51 ohms, L3—22 microhenries, D1 and D2—Type 2800—428 diodes (Hewlett Packard) R6—100,000 ohms, R7—750,000 ohms, R8—750,000 ohms, R9—51 ohms, Q3 and Q4—Type 2N3906 Transistors (Fairchild) R10—4,700 ohms, R11—51 ohms, R12—4,700 ohms, R13—8,200 ohms, R14—1,000,000 ohms, R15—100,000 ohms.

It should be noted that the effective capacitance that allows the dip oscillator to oscillate at the predetermined resonant frequency is 20 picofarads to which C1 and C2 contribute as does the "stray" capacitance in the circuit.

The collector of Q3 is capacitively coupled to Darlington connected amplifier Q5 for amplification. D3 keeps the low level radio frequency voltage and noise from reaching Q6 while C6 filters out the unwanted transients.

Q7 is a programmable uni-junction transistor connected as a timer whose time constant is established by R23 and C7. The adjustable R23 allows timing cycles from approximately 2 seconds to 30 seconds. When Q7 times out, Q8 is triggered on thereby activating light L as switch SW is normally closed. To prevent Q7 from timing out, C7 may be discharged by Q6 thereby preventing the SCR, Q8, from being triggered. Q6 conducts and discharges the charge in C7 when a dip signal comes from the collector of Q3, is differentiated by C5 and amplified by Q5.

The circuit values of the circuit elements shown in FIG. 5 are: L4—100 microhenries, C5—10 microfarads, R16—10 ohms, R17—750,000 ohms, R18—1,100 ohms, Q5—Type 2N5308 amplifier (Motorola) R19—100 ohms, R20—10,000 ohms, R21—2,200 ohms, D3—Type 1N914A diode (Continental Device) C6—0.047 microfarads, Q6—Type 2N3904 Transistor (Fairchild) R24—27 ohms, R25—62,000 ohms, R26—910,000 ohms, Q8—Type HEP R1215 SCR (Motorola).

A second assembly suitable for use in monitoring respiration and detecting apnea in a subject is shown generally in FIG. 10. A generating means, generally indicated at 110, generates an electromagnetic field having an output frequency in a predetermined frequency range about the subject. A passive circuit means, generally indicated at 112, has a resonant frequency variable in the predetermined frequency range of the generating means 110. The passive circuit means 112 is responsive to the electromagnetic field when the resonant frequency matches the frequency of the electromagnetic field. The same transducer or force transfer means illustrated in FIGS. 1 and 6 could be used for varing the resonant frequency of the passive circuit means 112 in response to the force exerted on the band 14 by the expansion and contraction of the chest 16 of the infant 18 during breathing.

The assembly also includes a detecting means, generally indicated at 120, which is responsive to the generating means 110 and detects when the passive circuit means 112 is responsive to the electromagnetic field. The detecting means 120 includes reset timing means such as reset timing circuit 122 which provides a first signal when the passive circuit means 112 fails to respond to the electromagnetic field at different, i.e., varying or changing, resonant frequencies within the predetermined frequency range within a predetermined time period and for reestablishing the predetermined time period as the resonant frequency of the passive circuit 112 continues to vary within the predetermined frequency range whereby the signal is provided in the event the subject fails to breathe within the predetermined time period.

The reset timing circuit may be substantially the same as the reset timing circuit 22 described above and the passive circuit means 112 may be substantially the same as the passive circuit means 12 described above.

The generating means 110 includes oscillator means such as the voltage controlled oscillator 136. The oscillator 136 is a variable frequency dip oscillator wherein the frequency is varied cyclically, i.e., the oscillator 136 is a swept frequency dip oscillator. The oscillator 136 acts as a conventional dip oscillator and displays the same drop in radio frequency current when a passive resonant circuit such as 112 couples to the oscillator 136 tank circuit. Naturally, the dip will occur only when the output frequency of the oscillator 136 passes through or matches the resonant frequency of the passive circuit means 112.

Also included in the generating means 110 is the frequency control means or sweep generator 137 for varying the output frequency of the oscillator 136 within a predetermined frequency range. The sweep generator 137 produces a saw-toothed wave form which programs the frequency of the oscillator 136. A convenient period may be from 0.1 to 1.0 seconds. The generating means 110 also includes a coil means such as sensing coil 138. Whereas, the dip oscillator 36 in the first embodiment oscillates at a predetermined constant frequency, the oscillator 136 in the second embodiment illustrated in FIG. 10 oscillates through a constantly changing or varying output frequency. The sensing coil 138 is coupled to the oscillator 136 so as to be responsive to the oscillator 136 when coupled thereto, that is, when the output frequency of the oscillator 136 matches the resonant frequency of the passive circuit means 112. As in the first embodiment, when the passive circuit means 112 is coupled to the electromagnetic field generated by the generating means 110, the sensing coil 138 is coupled to the passive circuit means 112 by the electromagnetic field, as the coil 138 establishes the electromagnetic field about the passive circuit means 112.

The detecting means 122 includes a differentiator 142 which may be similar to the differentiator 42 described above. The differentiator 142 is responsive to the increased coupling between the passive circuit means 112 and the sensing coil 138. The differentiator consists of an amplifier and a differentiation circuit for detecting and conditioning the dip pulse output from the oscillator 136, the dip pulse occurring when the resonant frequency of the passive circuit 112 matches the output frequency of the oscillator 136. Like in the first embodiment, the differentiator 142 compares the energy of the electromagnetic field before the increased coupling between the passive circuit means 112 and the sensing coil 138 to the energy of the electromagnetic field after the increased coupling, and generates a signal proportional to this difference.

The detecting means 120 further includes an average slope differentiator and comparator 143. The conditioned dip pulses received from the differentiator 142 trigger a sample and hold circuit in the differentiator and comparator 143 with this circuit's input being derived from the sweep generator 137.

Figure 11:
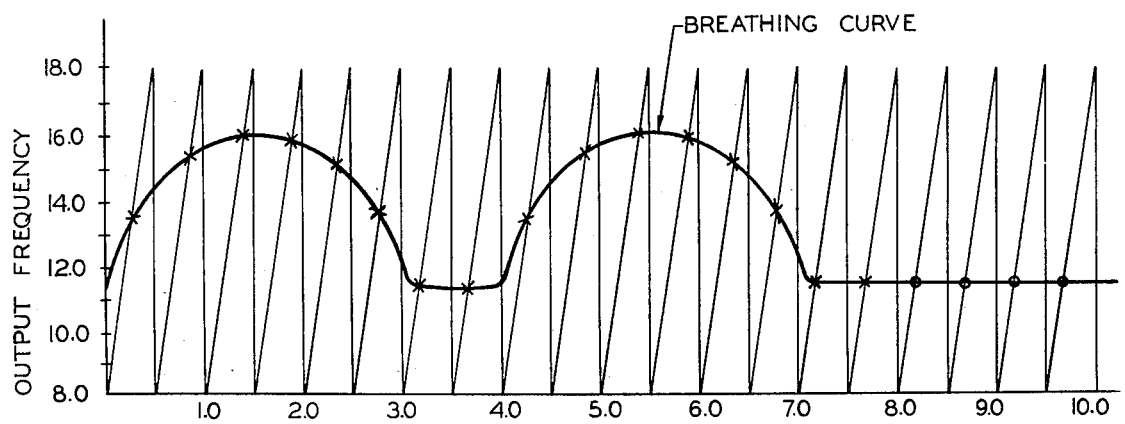
FIG. 11 is a graph showing a typical breathing curve imposed over a curve showing the variable frequency of the electromagnetic field established by the coil means of the embodiment of FIG. 10.

The graph in FIG. 11 illustrates on the vertical the predetermined frequency range of the output frequency of the oscillator 136. As illustrated, the output frequency of the oscillator 136, which is controlled by the sweep generator 137, is shown on the Y axis and is in a predetermined range between 8 and 18 megahertz. The X axis illustrates time in seconds. It will be understood that during each second the output frequency of the generating means 110 goes from 8 megahertz to 18 megahertz and then suddenly drops to 8 megahertz and then sweeps back to 18 megahertz, then again drops to 8 megahertz, i.e., two complete cycles per second. Thus, the output frequency of the generating means 110 continually varies between 8 and 18 megahertz, a predetermined or preselected frequency range.

Superimposed over the output frequency is a breathing curve which shows or illustrates inhalation, exhalation, a short pause followed by inhalation and exhalation. The breathing curve coincides with the variance of the resonant frequency of the passive circuit 112. As the curve illustrates, the resonant frequency of the passive circuit means 112 varies between approximately 12 megahertz and 16 megahertz which is within the predetermined range of the varying output frequency of the generating means 110. Each X indicating where the breathing curve intercepts the output frequency curve represents a point at which the resonant frequency of the passive circuit means 112 coincides, is coupled with, or matches the output frequency of the generating means 110, i.e., the oscillator 136. It will be observed that the coupling frequency between the passive circuit means 112 and the generating means 110 continually changes, as indicated by the X's in FIG. 11. The little zeros marking the intersection of the breathing curve and the output frequency curve indicate a cessation of breathing resulting in the passive circuit means 112 remaining at a fixed resonant frequency because of no chest movement of the subject. The breathing curve, so long as breathing is occurring as illustrated in FIG. 11, continually changes in slope but when breathing stops the slope does not change, as illustrated to the right of FIG. 11.

FIG. 12 is a graph showing again the output frequency of the generating means 110 on the Y axis with time in seconds on the X axis and superimposed thereover a slope curve indicating a continued increase in the slope of the breathing curve between the adjacent X's shown on the curve of FIG. 11, as through two seconds of exhalation, with the point 150 indicating a cessation in breathing with thereafter the slope of the breathing curve being constant, as indicated by the zero intersections in FIG. 11.

Figure 12:
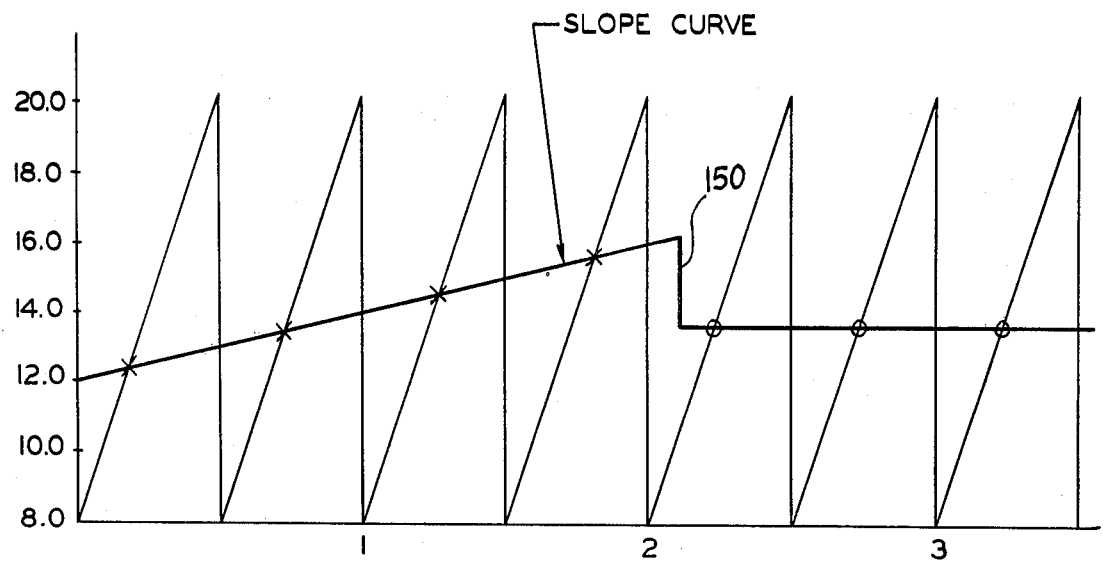
FIG. 12 is a graph showing the curve of the variable frequency of the electromagnetic field established by the coil means of the embodiment of FIG. 10 with a curve illustrating the passive circuit response signal showing a cessation of breathing imposed thereon.
Figure 13:
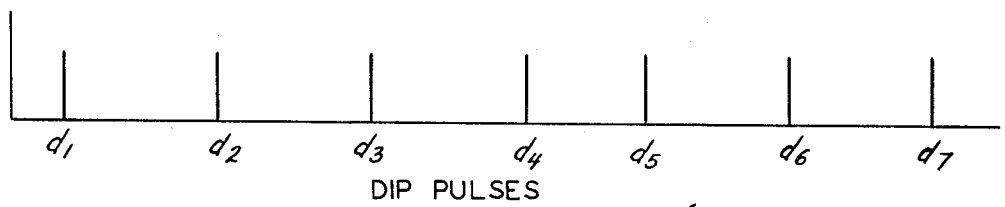
FIG. 13 is a diagram showing the pulses, each of which results from the passive circuit being responsive to the frequency of the electromagnetic field.

FIG. 13 shows the dip pulses which are generated at the intersection of the slope curve of FIG. 12 with the output frequency curve at the X's and zeros in FIG. 12.

Figure 14:
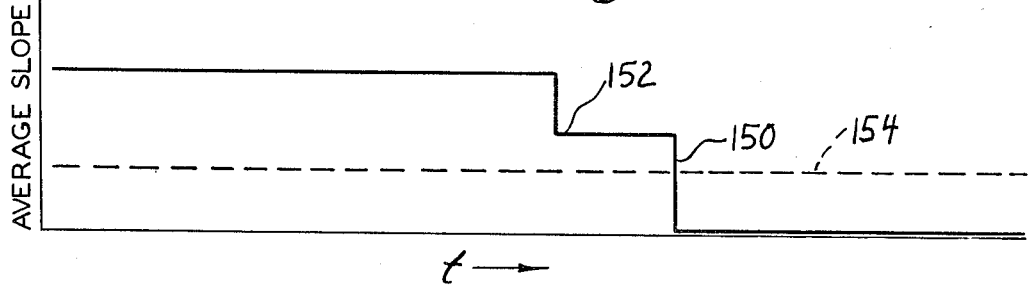
FIG. 14 is a diagram showing the average slope of the curve of FIG. 12, which illustrates the passive circuit response signal between the pulses shown in FIG. 13.

FIG. 14 is a graph illustrating the mathematical first derivative of the slope curve in FIG. 12 showing the average slope on the Y axis. The average slope differentiator 143 receives the dip pulses and an input from the sweep generator 137. The circuit 143 averages the slope of the slope curve shown in FIG. 12 between dip pulse intercepts as illustrated in FIG. 13. It then produdes an output as illustrated in FIG. 14. The step 152 in FIG. 14 represents the average slope of the slope curve shown in FIG. 12 between the X and the zero immediately on either side of the stop point 150. The comparative part of the circuit 143 also sets the trigger level which is indicated at 154. In other words, the average slope between dip pulses must drop below the value indicated at 154 which is built into the circuit 143. The value 154 is above zero to account for circuit noise and circuit variability as the circuit could change ever so slightly. The comparator monitors the change in the average slope level indicated in FIG. 14 with the comparator reference voltage level established at some nominal level 154 above zero. This level 154 may be adjusted in terms of sensitivity so that when the average slope falls below this threshold level, the timer circuit 122 is activated. As illustrated in FIG. 14, the average slope of the slope curve in FIG. 12 along the curve where the zeros indicate the intersection, drops to zero at the point 150 in FIG. 14. The reset timing circuit establishes a predetermined time period, one that would account for normal, sporadic or natural interruption of breathing so that if the comparator provides a signal indicating that there is less than the preset slope level as shown to the right of the point 150 in FIG. 14, the timing circuit would not provide a signal unless that slope level remains below the predetermined level 154 for a period of time established by the timing circuit, i.e., six seconds, in which case the alarm circuit 144 would be triggered. The reset timing circuit 122 may be substantially similar to the circuit 22 described above.

Thus, the generating means 110 includes a swept frequency dip oscillator 136 which provides an output frequency in a predetermined frequency range which would be certain to cover any possible resonant frequency of the passive circuit means 112, i.e., 8 to 18 or 20 megahertz whereas the passive circuit means moves between either 11 or 12 and 16 megahertz. So long as breathing continues, the frequency at which the passive circuit means 112 is resonant and coupled with the output frequency of a generating means 110 will continually change. So long as this change (i.e., curve slope, plus or minus) occurs, there will be no alarm signal. However, should breathing cease, the passive circuit means 112 will continually be resonant with the output frequency of the generating means 110 at a constant frequency which is sent by the detecting means 120 and, specifically, by the average slope differentiator and comparator 143. If that resonant frequency remains substantially constant for a period of time which exceeds a predetermined time set by the reset timing circuit 122, a signal is sent to the alarm circuit 144 and the alarm is sounded.

In accordance with the embodiment of FIG. 10, there is no criticality in adjusting the passive circuit means 112 to operate within a narrow band because the dip oscillator 136 continually sweeps over a relatively large band which is predetermined to definitely include the band over which the resonant frequency of the passive circuit means 112 oscillates.

The oscillator 136 may be one of many well known types including a type MC 1648, Motorola voltage controlled oscillator integrated circuit connected as per application note appearing in "MECL Integrated Circuits" (Motorola) Vol. 4, Series A, Section 6, page 10. The generator 137 may also be one of many well known types including an NE 555 timer I.C. connected as shown on page 62 of "555 Timer Applications Sourcebook", H. M. Berlin, Howard W. Sanis & Co., Inc., 1978. The differentiator 143 may be one of many well known types including the circuit shown on page 507 in "Electronics Circuits Manual" by J. Markus; McGraw-Hill Book Company, 1971.

It should be understood that this invention is not limited to the remote monitoring of respiration in human subjects. It is also envisioned that the instant invention may be modified whereby forces and/or motion may be monitored in a defined space without providing a transmitting device within the defined space. For example, irregularities in the motion of a reciprocating piston can be remotely sensed without requiring the human operator to enter the area of operation.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

The embodiments of the invention in which an exclusive property or privilege is claimed are defined as follows:

1. An assembly suitable for use in monitoring respiration and detecting apnea in a subject comprising; generating means for generating an electromagnetic field having an output frequency in a predetermined frequency range about the subject, passive circuit means having a resonant frequency variable in said predetermined frequency range and being responsive to said electromagnetic field when said resonant frequency matches said output frequency, transducer means adapted for attachment to the subject for varying said resonant frequency of said passive circuit means in response to the force exerted on said means for varying said resonant frequency by the expansion and contraction of that portion of the subject which expands and contracts during breathing, and detecting means responsive to said generating means for detecting when said passive circuit means is responsive to said electromagnetic field including reset timing means for providing a signal when said passive circuit means fails to respond to said electromagnetic field within a predetermined time period upon each occurrence of said passive circuit means being responsive to said electromagnetic field whereby said signal is provided in the event the subject fails to breathe within said predetermined time period.

2. An assembly as defined in claim 1 wherein said output frequency is maintained constant by said generating means.

3. An assembly as defined in claim 1 including frequency control means for varying said output frequency within said predetermined frequency range and wherein said reset timing means provides said signal when said passive circuit means fails to respond to said electromagnetic field at different frequencies within said predetermined frequency range within a predetermined time period and for reestablishing said predetermined time period as said resonant frequency continues to vary within said predetermined frequency range whereby said signal is provided in the event the subject fails to breathe within said predetermined time period.

4. A method of monitoring respiration and detecting apnea in a subject such as a human comprising the steps of; generating an electromagnetic field having an output frequency in a predetermined frequency range about the subject, absorbing electromagnetic energy from the electromagnetic field at said output frequency with a passive circuit energy absorber having a resonant frequency variable in said predetermined frequency range and varying said resonant frequency in response to the expansion and contraction of that portion of the subject which expands and contracts during breathing so that the electromagnetic energy of the electromagnetic field is absorbed when the resonant frequency matches the output frequency, detecting the absorption of energy from the electromagnetic field, providing an alarm signal in response to the lack of the absorption of energy from said electromagnetic field within a predetermined time period, the alarm being provided in the event the subject fails to breathe within the predetermined time period.

5. A method as defined in claim 4 including reestablishing the predetermined time period after detecting the absorption of energy from the electromagnetic field.

6. A method as defined in claim 5 further defined as manitaining said output frequency constant.

7. A method as defined in claim 5 further defined as varying said output frequency in said predetermined frequency range.

8. A method as defined in claim 7 including the step of providing the alarm signal in response to the lack of absorption of energy from the electromagnetic field at different resonant frequencies within the predetermined frequency range within the predetermined time period.

* * * * *